United States Patent [19]
White et al.

[11] Patent Number: 5,447,712
[45] Date of Patent: Sep. 5, 1995

[54] METHOD OF REDUCING CYCLOPHOSPHAMIDE INDUCED HEMORRHAGIC CYSTITIS

[75] Inventors: Randy D. White, Crystal Lake; Joseph A. Safron, Grayslake; Donovan E. Gordon, Highland Park; Deborah Rice, Broadview, all of Ill.

[73] Assignee: Free Radical Sciences, Cambridge, Mass.

[21] Appl. No.: 164,069

[22] Filed: Dec. 9, 1993

[51] Int. Cl.$^6$ ................... A61K 31/425; A61K 49/00
[52] U.S. Cl. ................... 514/110; 514/369; 514/922; 514/974; 514/90
[58] Field of Search ................... 514/369; 424/10

[56] References Cited

U.S. PATENT DOCUMENTS

| | | | |
|---|---|---|---|
| 2,712,202 | 7/1955 | Hosler et al. | 47/57.5 |
| 3,737,536 | 6/1973 | Sagner et al. | 424/246 |
| 3,755,578 | 8/1973 | McFarland et al. | 424/246 |
| 4,175,130 | 11/1979 | Yamanaka et al. | 424/270 |
| 4,335,210 | 7/1982 | Meister et al. | 435/113 |
| 4,338,315 | 7/1982 | Paget et al. | 424/246 |
| 4,398,026 | 8/1983 | Takano | 544/133 |
| 4,420,479 | 12/1983 | Morwick et al. | 424/246 |
| 4,434,158 | 2/1984 | Meister | 424/94 |
| 4,438,124 | 3/1984 | Meister | 424/270 |
| 4,563,471 | 1/1986 | Satzinger et al. | 514/369 |
| 4,647,453 | 3/1987 | Meisner | 424/54 |
| 4,647,571 | 3/1987 | Meister | 514/369 |
| 4,665,082 | 5/1987 | Meister et al. | 514/365 |
| 4,710,489 | 12/1987 | Meister | 514/18 |
| 4,752,618 | 7/1988 | Mascioli et al. | 514/549 |
| 4,775,675 | 10/1988 | Gyorgydeak et al. | 514/305 |
| 4,780,475 | 10/1988 | Cerra et al. | 514/408 |
| 4,784,685 | 11/1988 | Meister | 71/106 |
| 4,791,125 | 12/1988 | Clark | 514/369 |
| 4,798,835 | 1/1989 | Krupp et al. | 514/369 |
| 4,839,387 | 7/1989 | Poli | 514/19 |
| 4,868,114 | 9/1989 | Nagasawa et al. | 435/112 |
| 4,879,370 | 11/1989 | Meister | 530/331 |
| 4,963,577 | 10/1990 | Schorlemmer et al. | 514/369 |
| 5,002,953 | 3/1991 | Hindley | 514/275 |
| 5,028,627 | 7/1991 | Kilbourn et al. | 514/565 |
| 5,039,609 | 8/1991 | Klein | 435/68.1 |
| 5,053,387 | 10/1991 | Alexander | 514/2 |
| 5,055,446 | 10/1991 | Alexander et al. | 514/2 |
| 5,089,268 | 2/1992 | Katz | 424/450 |
| 5,095,027 | 3/1992 | Goldberg et al. | 514/369 |
| 5,158,883 | 10/1992 | Griffith | 435/240.2 |
| 5,208,249 | 5/1993 | Rowe et al. | 514/369 |
| 5,214,062 | 5/1993 | Mark et al. | 514/369 |

FOREIGN PATENT DOCUMENTS

| | | |
|---|---|---|
| 0002978 | 12/1978 | European Pat. Off. . |
| 0257992 | 3/1988 | European Pat. Off. . |
| 0318330 | 5/1989 | European Pat. Off. . |
| 0327263A1 | 8/1989 | European Pat. Off. . |
| 0338459A2 | 10/1989 | European Pat. Off. . |
| 0373002 | 6/1990 | European Pat. Off. . |
| 0374390 | 6/1990 | European Pat. Off. . |
| 0415598A1 | 3/1991 | European Pat. Off. . |
| 2141765 | 3/1973 | Germany . |
| 47-8537 | 11/1972 | Japan . |
| 8403625 | 9/1984 | WIPO . |
| 91/14424 | 3/1991 | WIPO . |
| 93/11104 | 11/1991 | WIPO . |

OTHER PUBLICATIONS

Mitchell et al., Br. J. Cancer Suppl. VIII (1987 Jun.) pp. 96–104. Ref: 38.

Bounous, et al., *Immunoenhancing Property of Dietary Whey Protein in Mice, Role of Glutathoine*, Clinical Investigative Medicine, vol. 12, No. 4, pp. 154–161. 1989.

(List continued on next page.)

*Primary Examiner*—Raymond Henley, III
*Assistant Examiner*—Phyllis G. Spivack
*Attorney, Agent, or Firm*—Pennie & Edmonds

[57] ABSTRACT

A method is provided for reducing side effects caused by chemotherapeutic agents by administering to a patient in need thereof a therapeutically effective amount of a composition including L-2-oxothiazolidine-4-carboxylate specifically for reducing hemorrhagic cystitis in a patient at risk of same.

17 Claims, 4 Drawing Sheets

OTHER PUBLICATIONS

Suthanthiran, et al., *Glutathione Regulates Activation-Dependent DNA Synthesis in High Purified Normal Human T Lymphocytes Stimulated via the CD2 and CD3 Antigens,* Proc. of National Academic Sciences, vol. 37, May 1990, pp. 3343-3347.

Chung, et al., *L-2-Oxothiazolidine-4-Carboxylate as a cysteine Precursor: Efficacy for Growth and Hepatic Glutatione Synthesis in Chicks and Rats,* American Institute of Nutrition, pp. 158-165. 1989.

Mandel, et al. *Intracellular Gluthathione in the Protection from Anoxic Injury in Renal Proximal Tubles,* J. Clin. Invest., 1990 vol. 85, No. 2, pp. 316-324.

Chang, et al., *Cytoprotective Effect of Reduced Glutathione in Arsenical-Induced Endothelial Cell Injury,* Toxicology, 1991, vol. 69, No. 1, pp. 101-110.

Moslen, *Protection by L-2-Oxothiazolidine-4-Carboxylate, a Cysteine Prodrug, Against 1,1-Dichlorethylene Hepatotoxicity in Rats is Associated with Decreased in Toxin Metabolism and Cytochrome P-450,* J. Pharmacol. Exp. Ther., vol. 248, No. 1, pp. 157-163. 1989.

Cretton, et al., *Catabolism of 3'-Axido-3'Deoxythymidine in Hepactocytes and Liver Microsomes, with Evidence of Formation of 3'-Amino-3'Deoxythymidine, a Highly Toxic Catabolite for Human Bone Marrow Cells,* Molecular Pharmacology, Vo. 39, pp. 258-266. 1990.

Handlon, et al., *Thiol Reduction of 3'-Aziodthymidine to 3'-Aminothymidine: Kinetics and Biomedical Implications,* Pharmaceutical Research, vol. 5, No. 5, pp. 297-299, 1987.

Lamperth, et al. *Abnormal Skeletal and Cardiac Muscle Mitochondria Induced by Zidovudine (AZT) in Human Muscle In vitro and in an Animal Model,* Laboratory Investigation, vol. 65, No. 6, pp. 742-752. 1991.

Bone, et al., *Definitions for Sepsis and Organ Failure,* Critical Care Medicine, 1992, vol. 20, No. 6, pp. 724-725.

American College of Chest Physicians/Society of Critical Care Medicine Consensus Conference Committee, *American College of Chest Physicians/Society of Critical Care Medicine Consensus Conference: Definitions for Sepsis and Organ Failure and Guidelines for the Use of Innovative Therapies in Sepsis,* Critical Care Medicine, Jun. 1992, vol. 20, No. 6, pp. 864-874.

Kilbourn, et al., *Inhibition of Interleukin-1-α-Induced nitric Oxide Synthase in Vascular Smooth Muscle and Full Reversal of Interleukin-1-α Induced Hypotension by $N^{\omega}$-Amino-L-Arginine,* Journal of the National Cancer Institute, Jul. 1, 1992, vol. 84, No. 13, pp. 1008-1016.

Osol, et al., EDs., *Remington's Pharmaceutical Sciences,* 1980, Sixteenth Edition.

W. Lucht et al, *Prevention of Release of Granulocyte Aggregants into Sheep Lung Lymph Following Endotoxemia by N-Acetylcysteine,* The American Journal of the Medical Sciences, vol. 294, No. 3, Sep. 1987, pp. 161-167.

G. Bernard et al, *Effect of N-Acetylcysteine on the Pulmonary Response to Endotoxin in the Awake Sheep and Upon In Vitro Granulocyte Function,* J. Clin. Invest., vol. 73, Jun. 1984, pp. 1772-1784.

A. Cantin et al, *Normal Alveolar Epithelial Lining Fluid Contains High Levels of Glutathione,* pp. 152-157. 1987.

L. Smith et al, *Effect of Fasting on Hyperoxic Lung Injury in Mice,* Am. Rev. Respir. Dis. 1990; 141:141-149.

J. Strausz et al, *Oxygen Radical Production by Alveolar Inflammatory Cells in Idiopathic Pulmonary Fibrosis,* Am. Rev. Respir. Dis. 1990; 141:124-128.

A. Cantin et al, *Glutathione Deficiency in the Epithelial Lining Fluid of the Lower Respiratory Tract in Idiopathic Pulmonary Fibrosis,* Am. Rev. Respir. Dis. 1989; 139:370-372.

*Guarding Against Cellular Glutathione Deficiency,* Nutrition Reviews, vol. 48, No. 9, Sep. 1990, pp. 346-348.

A. Cantin et al, *Oxidants, Antioxidants and the Pathogenesis of Emphysema,* Eur. J. Respir. Dis (1985) 66, Suppl. 139, pp. 7-17.

I. Cotgreave et al, *Lung and Systemic Thiol Homeostasis During an Acute Lung Inflammation in the Rat,* Toxicology, 50 (1988), pp. 331-343.

J. Sun et al, *Effects of Buthionine Sulfoximine on the Development of Ozone-Induced Pulmonary Fibrosis,* Experimental and Molecular Pathology 49 (1988), pp. 254-266.

S. Baldwin et al, *Oxidant Activity in Expired Breath of Patients with Adult Respiratory Distress Syndrome,* The Lancet, Jan. 4, 1986, pp. 11-14.

(List continued on next page.)

OTHER PUBLICATIONS

M. F. Tsan et al, *Enhancement of Intracellular Glutathione Protects Endothelial Cells Against Oxidant Damage*, Biochemical and Biophysical Research Communications, vol. 127, No. 1, Feb. 28, 1985, pp. 270–276.

M. F. Tsan et al, *L-2-Oxothiazolidine-4-Carboxylate Protects Endothelial Cells Against Hyperocia–Induced Injury*, Inflammation, vol. 12, No. 2, 1988, pp. 113–121.

P. H. S. Sporn et al, *Complex Effects of In Vitro Hyperoxia on Alveolar Macrophage Arachidonic Acid Metabolism*, American Journal of Respiratory Cell and Molecular Biology, vol. 2, No. 1, Jan. 1990, pp. 81–90.

M. A. Passero et al, *L-2-Oxothiazolidine-4-Carboxylic Acid Increases Glutathione in Mouse Lung*, A. Rev. Respir. Dis., vol. 133, 1986, p. A395.

Bellin, et al., *Purification of Glycosaminoglycens from Bovine Follicular Fluid*, J. Dairy Sci., Nov. 9, 1987, vol. 70, pp. 1913–1919.

Calvin, et al., *Estimation and Manipulation of Glutathione Levels in Prepuberal Mouse Ovaries and Ova: Relevance to Sperm Nucleus Transformation in the Fertilized Egg*, Gamete Research, 1986, vol. 14, pp. 165–275.

Gordon, et al., *Applications of Micromanipulation to Human in Vitro Fertilization*, Journal of In Vitro Fertilization and Embryo Transfer, 1988, vol. 5, No. 2, pp. 57–60.

Perreault, et al., *Importance of Glutathione in the Acquisition and Maintenance of Sprem Nuclear Decondensing Activity in Maturing Hamster Oocytes*, Developmental Biology, 1988, vol. 125, pp. 181–186.

Perreault, et al., *The Timing of Hamster Sperm Nuclear Decondensation and Male Pronucleus Formation is Related to Sperm Nuclear Disulfide Bond Content*, Biology of Reproduction, 1987, vol. 36, pp. 239–244.

Perreault, et al., *The Role of Disulfide Bond Reduction During Mammalian Sperm Nuclear Decondensation in Vivo*, Developmental Biology, 1984, vol. 101, pp. 160–167.

Reyes, et al., *Heparin and Glutathione: Physiological Decondensing Agents of Human Sperm Nuclei*, Gamete Research, 1989, vol. 23, pp. 39–47.

Zirkin, et al., *In Vitro and In Vivo Studies of Mammalian Sperm Nuclear Decondensation*, Gamete Research, 1985, vol. 11, pp. 349–365.

Shapiro, *The Control of Oxidant Stress at Fertilization*, Science, Apr. 26, 1991, pp. 533–536.

Slaweta, et al., *The Effect of Glutathioine on the Motility and Fertility of Frozen Bull Sperm*, Amin. Reprod. Sci., 1987, vol. 13, No. 4, pp. 249–253.

Perreault, et al., *Importance of Glutathione In the Acquisition And Maintenance of Sperm Nuclear Decondensing Activity In Maturing Hamster Oocytes*, Dev. Biol., 1988, vol. 125, No. 1, pp. 181–186.

Lassalle, et al., *Relationship Between Fertilizing Ability of Frozen Human Spermatozoa and Capacity for Heparin Binding and Nuclear Decondensation*, J. Reprod. Fertil, 1992, vol. 95, No. 2, pp. 313–324.

Wellman, et al., *Radioprotection by glutathione ester: Transport of glutathione ester into human lymphoid cells and fibroblasts*, Proc. Natl. Acad. Sci. USA, 1984, vol. 81, pp. 4732–4735.

Martenson, et al., *Glutathione metabolism in the lung: Inhibition of its synthesis leads to lamellar body and mitochondrial defects*, Proc. Natl. Acad. Sci. USA, 1989, vol. 86, pp. 5296–5300.

Roberts, et al., *Prodrugs of L-Cysteine as Protective Agents against Acetaminophen–Induced Hepatotoxicity. 2-(Polyhydroxyalkyl)-and 2-(Polyacetoxyalkyl)-thiazolidine-4(R)-carboxylic Acids*, J. Med. Chem. 1987, vol. 30, No. 10, pp. 1891–1896.

Astor, et al., *Relationship Between Intracellular 'GSH Levels and Hypoxic Cell Radiosensitivity*, Pharmac. Ther., 1988, pp. 115–121.

Martenson, et al., *Mitochondrial damage in muscle occurs after marked depletion of glutathione and is prevented by giving glutathione monoester*, Proc. Natl. Acad. Sci. USA, 1989, vol. 86, pp. 471–475.

Bounous et al., *The influence of dietary whey protein on . . . glutathione and the diseases of aging*, American Chemcial Society, CA 112. 1989.

Kuzuya, et al., *Protective role of intracellular glutathione against oxidized low density lipoprotein in cultured endothelial cells*, Biochem. Biophys. Res. Commun 163 (3) 1989.

Roseneld et al., *Macrophage–derived Foam Cells Freshly Isolated from Rabbit Atherosclerotic Lesions Degrade Modified Lipoproteins, Promote Oxidation of Low-Density Lipoproteins, and Contain Oxidation-specific Lip–-Protein Adducts*, The American Society for Clinical Investigation, Inc., 1991, vol. 87, pp. 90–99.

(List continued on next page.)

OTHER PUBLICATIONS

Heinecke, et al., *The Role of Sulfur-containing Amino Acids in Superoxide Production and Modification of Low Density Lipoprotein by Arterial Smooth Muscle Cells*, The Journal of Biologicla Chemistry, 1987, vol. 262, No. 21, pp. 10098–10103.

Parthasarathy, *Oxidation of low-density lipoprotein by thiol compounds leads to its recognition by the acetyl LDL receptor*, Biochimica et Biophysica Acta, 917, 1987, pp. 337–340.

Roederer, et al., *Cytokine-stimulated human immunodeficiency virus replication is inhibited by N-acetyl-L-cysteine*, Proc. Natl. Acad. Sci. USA, 1990, vol. 87, pp. 4884–4888.

Kalebic, et al., *Suppression of human immunodeficiency virus expression in chroniclaly infected monicytic cells glutathione, glutathione ester, and N-acetylcysteine*, Proc. Natl. Acad. Sci. USA, 1991.

Gustafson, et al., *Aids-Antiviral Sulfolipids from Cyanobacteria (Blue-Green Algae)*, J. Natl. Cancer Inst., 1989, vol. 81, No. 16, pp. 1254–1258.

Predergast, et al., *Arachidonic Acid-Biding Peptides, Antibodies Produced to these Peptides, and unsaturated Fatty Acid Compounds Having Affinity for the Peptides for Therapy, Pharmaceuticsl, and Product Sterilization*, Chemical Abstracts, 1992, vol. 116, p. 84.

Frankova, *The Effects of Amino Acids with Sulfhydryl Groups on Herpest Viruses in Vitro*, Acla Virol, Engl. Ed., (1967), vol. 11, No. 6, pp. 559–561.

Abate, et al. *Redox Regulation of Fos and Jun DNA--Finding Activity in Vitro*, Science, Sep. 1990, vol. 249, pp. 1157–1161.

Duh, et al. *Tumor Necrosis Factor α Activates Human Immunodeficiency Virus Type 1 through Induction of Nuclear Factor Binding to the NF-$_k$B Sites in the Long Terminal Repeat*, Proc. Natl. Acad. Sci. USA, Aug. 1989, vol. 86, pp. 5974–5978.

Staal, et al., *Intracellular Thiols Regulate Activation of Nuclear Factor $_k$B and Transcription of Human Immunodeficiency Virus*, Proc. Natl. Acad. Sci. USA, Dec. 1990, vol. 87, pp. 9943–9947.

Mihm, et al., *Inhibition of HIV-1 Replication and NF-$_x$B activity by Cysteine and Cysteine Derivatives*, Aids 1991, vol. V. No. 5, pp. 497–503.

Schnittman, et al., *The Reservoir for HIV-1 in Human Peripheral Blood is a T Cell that Maintains Expression of CD4*, Science, Jul. 21, 1989, vol. 245, pp. 305–308.

Peristeris, et al., *N-Acetylcystein and Glutathione as Inhibitors of Tumor Necrosis Factor Production*, Cell. Immunol., 1992, vol. 140, No. 2, pp. 390–399.

Keller, et al., *Decreased Hepatic Gluthatione Levesl in Septic Shock. Predisposition of Hepatocytes to Oxidative Stress: an Experimental Approach*, Arch. Surg. (Chicago), 1985, vol. 120. No. 8, pp. 941–945.

Pacht, et al., *Deficiency of Alveolar Fluid Glutathione in Patients with Sepsis and the Adult Respiratory Distress Syndrome*, Chest, 1991, vol. 100, No. 5, pp. 1397–1403.

Flaherty, et al., *Reperfusion Injury*, Free Radical Biology & Medicine, 1988, vol. 5, pp. 409–419.

Darley-Usmar, et al., *Oxygen and Reperfusion Damage: an Overview*, Free Radi. Res. Comms., vol. 7, No. 3–6, pp. 247–254. 1989.

Lachman, et al., The Theory and Practice of Industrial Pharmacy, 1976, 2nd Ed., pp. 513–524. 1976.

Bjelton, et al., *Availability of Cysteine and of L-2-Oxo-Thiazolidine-4-Carboxylic Acid as a Source of Cysteine in Intravenous Nurtrition*, J. Parenter Enteral Nutr., Mar.-Apr. 1990, vol. 14, No. 2, pp. 177–182.

Nappe, et al., *Electrophoretic Analysis of Alkylated Proteins of Human Hair from Various Ethnic Groups*, J. Soc. Cosmet, Chem., Mar./Apr. 1989, vol. 40, pp. 91–99.

Pruche, et al., *Chaanges in Glutathione Content in Human Hair Follicle Keratinocytes as a Function of Age of Donor: Relation with Glutathione Dependent Enzymes*, International Journal of Cosmetic Science, 1991, vol. 13, pp. 117–124.

Kermici, et al., *Evidence for an Age-Correlated Change in glutathione Metabolism Enzyme Activities in Human Hair Follicle*, Mechanisms of Ageing and Development, 1990, vol. 53, pp. 73–84.

Rao, et al., *Synthesis and Characterization of Defensin NP-1*, Int. J. Peptide Protein Res., 1992, vol. 40, pp. 507–514.

Angier, *From the body Itself, Hope for a New Breed of Potent Antibiotics*, New York Times, Feb. 26, 1991, pp. 26–27.

Levy, et al., *Transport of Glutathione Diethyl Ester into Human Cells*, Proc. Natl. Acad. Sci, USA, Oct. 1993, vol. 19, pp. 9171–9175.

Jimenez, et al., *Treatment with ImuVert/N-Acetylcysteine Protects Rats from Cyclophosphamide/Cytarabine-Induced Alopecia*, Cancer Investigation, 1992, vol. 10, No. 4, pp. 271–276.

METHOD OF REDUCING CYCLOPHOSPHAMIDE INDUCED HEMORRHAGIC CYSTITIS

BACKGROUND OF THE INVENTION

The present invention relates generally to the treatment of patients using chemotherapy agents. More specifically, the present invention relates to reducing or preventing side effects caused by chemotherapeutic agents.

Cancer can develop in any tissue of any organ at any age. Many cancers detected at an early stage are potentially curable. The principal objectives of cancer screening and early diagnosis are: (1) to decrease cancer mortality; (2) to lead to less radical therapy; and (3) to reduce financial costs. Merck Manual, 16th Edition, 1263, 1269 (1992).

Successful therapy must be focused on the primary tumor and its metastases, whether clinically apparent or microscopic. Thus, local and regional therapy, surgery, or radiation must be integrated with systemic therapy (e.g. drugs). Id. at 1275.

The ideal antineoplastic drug will destroy cancer cells without adverse effects or toxicities on normal cells. Unfortunately, no such drug exists. Id. at 1277. As a result, patients receiving antineoplastic drugs often must endure the toxic side effects of such drugs.

Among other chemotherapeutic/immunosuppressive drugs, cyclophosphamide is an essential component of many effective antineoplastic therapies. Cyclophosphamide has a very broad clinical spectrum of activity. Calabresi, P. and B. A. Chabner, Antineoplastic Agents: Cyclophosphamide, In, Goodman and Gilman's The Pharmacological Basis of Therapeutics, Eighth Edition, pp. 1216–1218 (1990). Because of its potent immunosuppressive properties, cyclophosphamide is used in controlling transplanted organ rejection and nonneoplastic immune disorders. In fact, cyclophosphamide, an oxazaphosphorine alkylating agent, is used in over 200,000 patients a year to treat neoplastic, immune mediated, and transplant related diseases.

Unfortunately, as with other chemotherapeutic/immunosuppressive drugs, cyclophosphamide has a significant dose dependent toxicity. See Physicians' Desk Reference, 44th Edition, p. 745 (1990). In addition, using cyclophosphamide results in a high potential for inducing sterility, teratogenic effects, mutations and cancer.

The occurrence of sterile, hemorrhagic cystitis is the most common therapy-limiting side effect of cyclophosphamide. Hemorrhagic cystitis occurs in up to 78% of the patients treated with cyclophosphamide. Grinbert-Funes, D. J., C. Sheldon, and M. Weiss, The Use of Prostaglandin $F_2$ Alpha for the Prophylaxis of Cyclophosphamide Induced Cystitis in Rats, 144(6) J Urology, pp. 1500–1504 (1990). Although the basis for the injury to the urinary system is not completely understood, cyclophosphamide metabolites excreted in the urine are thought to induce cystitis. Physicians' Desk Reference, p. 745. Specifically, an active metabolic product of cyclophosphamide, namely acrolein, is thought to cause hemorrhagic cystitis.

Several sulphur containing materials have shown some success in preventing or reducing hemorrhagic cystitis. Namely, researchers have reported the use of N-acetylcysteine, 2-mecapthoethane sulfonate (Mesna), disodium 2-2'-dithio-bis-ethane sulfonate (Dimesna), and reduced glutathione as having some effect in reducing this side effect. Grinbert-Funes, D. J., et al, supra, at 2; Habs M. R., et al, Prevention of Urinary Bladder Tumors in Cyclotphosphamide-Treated Rats by Additional Medication With the Uroprotectors Sodium 2-mercaptoethane Sulfonate (Mesna) and Disodium 2,2'-dithio-bis-ethane Sulfonate (Dimesna), Cancer 51:606–609 (1983); and Nobile, M. T., et al, A Preliminary Clinical Study of Cyclophosphamide With Reduced Glutathione as Uroprotector, Tumori 73(3): 257–258 (1989).

One of these compounds, Mesna, is a synthetic sulfhydryl compound and is currently marketed as Mesnex ® Injection. This Mesnex ® Injection product is marketed as a detoxifying agent to inhibit hemorrhagic cystitis. Mesna forms a nontoxic thioether with acrolein, and has an added inhibitory effect on the spontaneous release of acrolein from hydroxylated cyclophosphamide in urine. Rats given Mesna in conjunction with cyclophosphamide experienced a significant decrease in ulceration, inflammation and edema of the bladder compared to those treated with cyclophosphamide alone.

These known compounds suffer certain drawbacks. Further, these compounds do not address other side effects of chemotherapeutic treatment such as induction of cancer, alopecia and sterility.

SUMMARY OF THE INVENTION

The present invention provides a method for reducing or preventing side effects associated with chemotherapeutic agents. More specifically, the present invention provides a method for reducing or preventing side effects associated with the treatment of cyclophosphamide as well as preventing hemorrhagic cystitis that may be associated with the chemotherapeutic agents.

In an embodiment, the present invention provides a method for reducing or preventing hemorrhagic cystitis in a patient at risk of same. The method includes the step of administering to the patient a therapeutically effective amount of a composition including L-2-oxothiazolidine-4-carboxylate. In an embodiment, the patient is at risk of hemorrhagic cystitis due to the chemotherapeutic drug the patient is receiving.

In an embodiment, the chemotherapeutic drug is cyclophosphamide.

The present invention also provides a method for inhibiting the toxic side effects of cyclophosphamide. The method comprises a step of administering to a patient receiving the cyclophosphamide a therapeutically effective amount of a composition including L-2-oxothiazolidine-4-carboxylate.

Still further, the present invention provides a method for treating a patient who has hemorrhagic cystitis. The method comprises the step of administering to the patient a therapeutically effective amount of a composition including L-2-oxothiazolidine-4-carboxylate.

An advantage of the present invention is that it prevents or reduces hemorrhagic cystitis associated with chemotherapy. As a result, chemotherapeutic/immunosuppressive drugs, such as cyclophosphamide, can be more effectively used in the treatment of cancer.

Another advantage of the present invention is that it provides a new method for inhibiting toxic side effects associated with the use of cyclophosphamide.

Furthermore, an advantage of the present invention is that it provides a method for treating hemorrhagic cystitis.

Additional features and advantages of the present invention are described in, and will be apparent from, the detailed description of the presently preferred embodiments and from the drawings.

DETAILED DESCRIPTION OF THE PRESENTLY PREFERRED EMBODIMENTS

Hemorrhagic cystitis can occur due to a number of possible causes and insults. For example, hemorrhagic cystitis may develop in patients treated with cyclophosphamide. Cyclophosphamide causes a dose dependent toxicity. This dose dependency thereby limits the therapeutic approaches that can be taken with such a compound.

The inventors have surprisingly found that the use of a composition including L-2-oxothiazolidine-4-carboxylate when administered to a patient at risk of hemorrhagic cystitis will reduce or prevent such cystitis. In addition, the inventors believe the use of L-2-oxothiazolidine-4-carboxylate will inhibit other side effects suffered by patients receiving the cyclophosphamide drug.

L-2-oxothiazolidine-4-carboxylate is subjected to the action of 5-oxo-L-prolinase in the presence of triphosphate to produce S-carboxyl cysteine. S-carboxyl cysteine is then decarboxylated to produce cysteine. The cysteine is then metabolized to provide glutathione. See U.S. Pat. Nos.: 4,335,210; 4,434,158; 4,438,124; 4,665,082; and 4,647,571. The disclosures of these patents are incorporated herein by reference.

Likewise, esters of L-2-oxothiazolidine-4-carboxylate can be used. The ester can be saturated straight or branched, alkyl groups of 1 to 10 carbon atoms. Preferably, the ester is chosen from a saturated straight alkyl group such as methyl, ethyl, propyl, butyl, pentyl, hexyl, hepyl, octo, nonyl or dectyl and a saturated branched alkyl such as isopropyl, isobutyl, sec-butyl, tert-butyl, or isopenyl. Such esters are disclosed in U.S. Pat. No. 5,208,249. The disclosure of U.S. Pat. No. 5,208,249 is hereby incorporated herein by reference.

Pursuant to the present invention, the composition of the present invention can be either administered parenterally or enterally. Enterally, the composition can comprise a pill including the L-2-oxothiazolidine-4-carboxylate that is administered to a patient.

Parenterally, the composition can, for example, include approximately 3% to about 6%, by weight, L-2-oxothiazolidine-4-carboxylate in a buffer solution such as phosphate buffer. Of course, parenterally, the composition can be administered as a bolus or as an additive to an IV solution.

If the treatment is to prevent or reduce hemorrhagic cystitis caused by a chemotherapeutic drug, e.g., cyclophosphamide, the composition can be administered either contemporaneously with the agent or on the same day. Alternatively, if the composition is being used to treat hemorrhagic cystitis, the composition can be administered alone. Still further, the inventors envision that the composition can be part of the patient's diet.

By way of example, and not limitation, an example of the present invention will now be given.

EXAMPLE

An experiment was conducted to evaluate changes in bladder histology and hematology parameters following administration of a known urotoxic dose of cyclophosphamide in conjunction with the composition of the present invention. To assess the protective effect of the present invention, the composition including L-2-oxothiazolidine-4-carboxylate was compared to a known protective agent, 2-mercaptoethane sodium sulfonate (Mesna).

Clintec Nutrition Company, Deerfield, Ill., provided the L-2-oxothiazolidine-4-carboxylate (Procysteine ®). The control diet consisted of no Mesna or Procysteine ®.

Forty-eight, male Sprague-Dawley rats were studied. The rats were divided into eight groups. Each group identifies a specific type of treatment. Table 1 below identifies these various groups and the specific type of treatment administered to the various rats.

TABLE 1

| | Treatment Regimens | | |
|---|---|---|---|
| Group | Treatment | Procedure | No. of Animals |
| 1 | Untreated | None | 6 |
| 2 | Mesna | 21.5 mg/kg, i.p. (Day −1 and Day 0) | 6 |
| 3 | Procysteine ® | 100 mg/kg, p.o. (Day −1 and Day 0) | 6 |
| 4 | CP | 68 mg/kg, i.v. (Day 0) | 6 |
| 5 | CP + Procysteine ® | 68 mg/kg, i.v. (Day 0) 100 mg/kg, p.o (Day −1 and Day 0) | 6 |
| 6 | CP + Mesna | 68 mg/kg, i.v. (Day 0) 21.5 mg/kg, i.p. (Day −1 and Day 0) | 6 |
| 7 | CP + Procysteine ® | 68 mg/kg, i.v. (Day 0) 1 g/kg, p.o. (Day −1, Day 0 and Day 1) | 6 |
| 8 | CP + Procysteine ® | 68 mg/kg, i.v. (Day 0) 1 g/kg, i.p. (Day −1, Day 0 and Day 1) | 6 |

Rats in group 1 received no treatment. Rats in Groups 2 and 6 were given Mesna once on Day 1 and on Day 0. Rats in Groups 3 and 5 were given Procysteine ® once on Day-1 and on Day 0. Rats in Group 4 were treated with cyclophosphamide alone. Rats in Groups 7 and 8 were given Procysteine ® twice a day on Day −1, Day 0 and Day 1. In all groups receiving dual treatment, cyclophosphamide doses were given on Day 0, thirty minutes prior to Procysteine ® or Mesna administration.

Forty-eight hours after cyclophosphamide injection, blood and bladder samples were taken for evaluation. Hematology was determined using a Sysmex ® Hematology Analyzer. White blood cell differentials were counted manually. Bladder samples were fixed in 10% buffered formalin, processed and stained with hematoxylin and eosin. Severity of cystitis was then graded on a scale of 0 to 5.

RESULTS AND ANALYSIS

Figure 1:
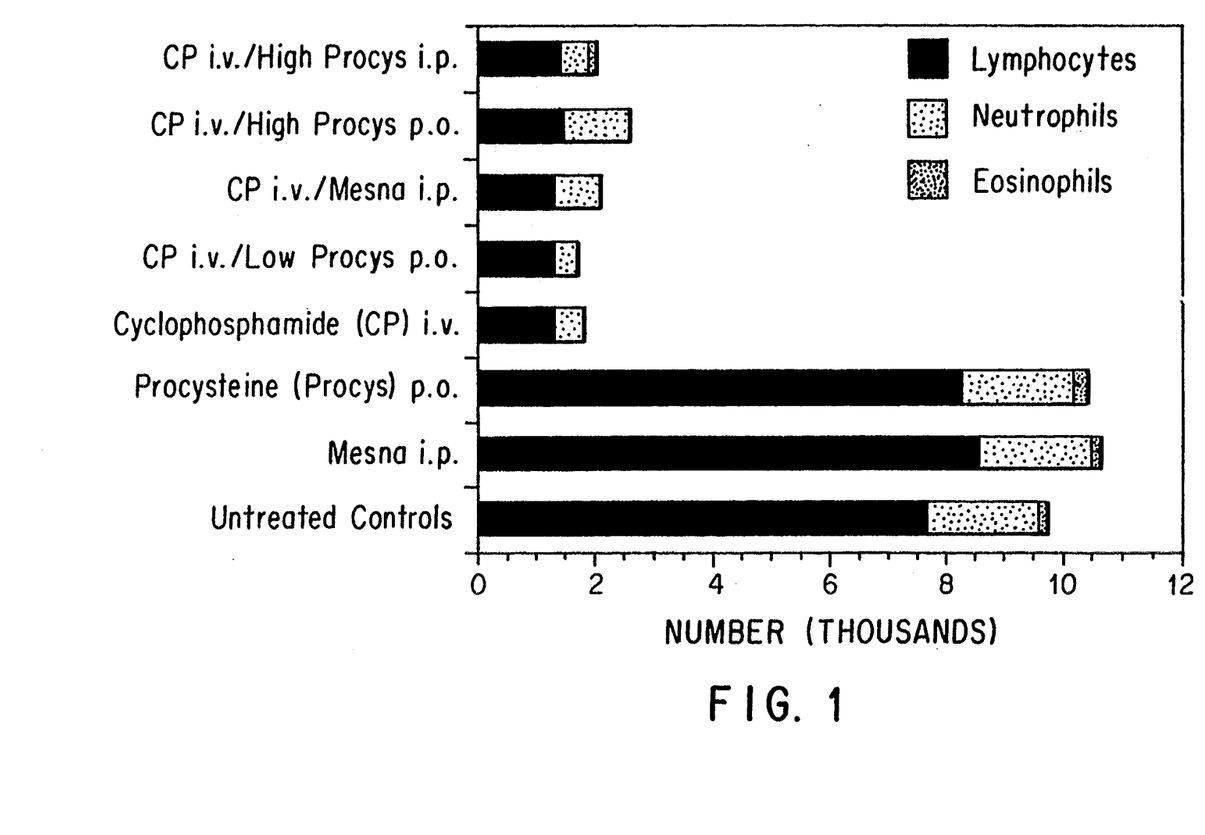
FIGS. 1-2 illustrate, graphically, the results of experiments conducted in an example of the present invention.

Hematology parameters were first evaluated. All animals that received cyclophosphamide experienced a panleukopenia. No differences existed between the cyclophosphamide treated groups. FIG. 1 illustrates the observed mean leukocyte values for the eight treatment groups.

As Table 2 below details, no treatment regimens affected red blood cell count, hemoglobin concentration, hematocrit or platelet count.

TABLE 2

| Group | Treatment | RBC [Million/μl] | HGB [g/dL] | HCT [%] | Platelet [Thou/ul] |
|---|---|---|---|---|---|
| 1 | Untreated[a] | 7.47 ± 0.33 | 15.2 ± 0.72 | 42.6 ± 1.48 | 906 ± 139.7 |
| 2 | Mesna i.p.[a] | 7.31 ± 0.25 | 14.9 ± 0.61 | 41.9 ± 1.51 | 941 ± 173.2 |
| 3 | Low Procysteine p.o.[a] | 7.28 ± 0.31 | 15.2 ± 0.39 | 43.1 ± 1.60 | 948 ± 93.3 |
| 4 | CP i.v.[b] | 7.99 ± 1.31 | 16.3 ± 2.58 | 45.8 ± 7.72 | 939 ± 332.6 |
| 5 | CP i.v./Low Procysteine p.o.[a] | 7.25 ± 0.89 | 15.2 ± 1.79 | 42.8 ± 5.05 | 820 ± 143.9 |
| 6 | CP i.v./Mesna i.p.[a] | 7.26 ± 0.37 | 15.0 ± 0.63 | 41.9 ± 1.94 | 794 ± 251.5 |
| 7 | CP i.v./High Procysteine p.o.[b] | 7.8 ± 0.66 | 15.8 ± 0.84 | 43.7 ± 3.22 | 781 ± 133.8 |
| 8 | CP i.v./High Procysteine i.p.[a] | 7.2 ± 0.50 | 15.0 ± 0.79 | 42.5 ± 2.67 | 799 ± 96.2 |

[a] n = 6
[b] n = 5

Figure 2:
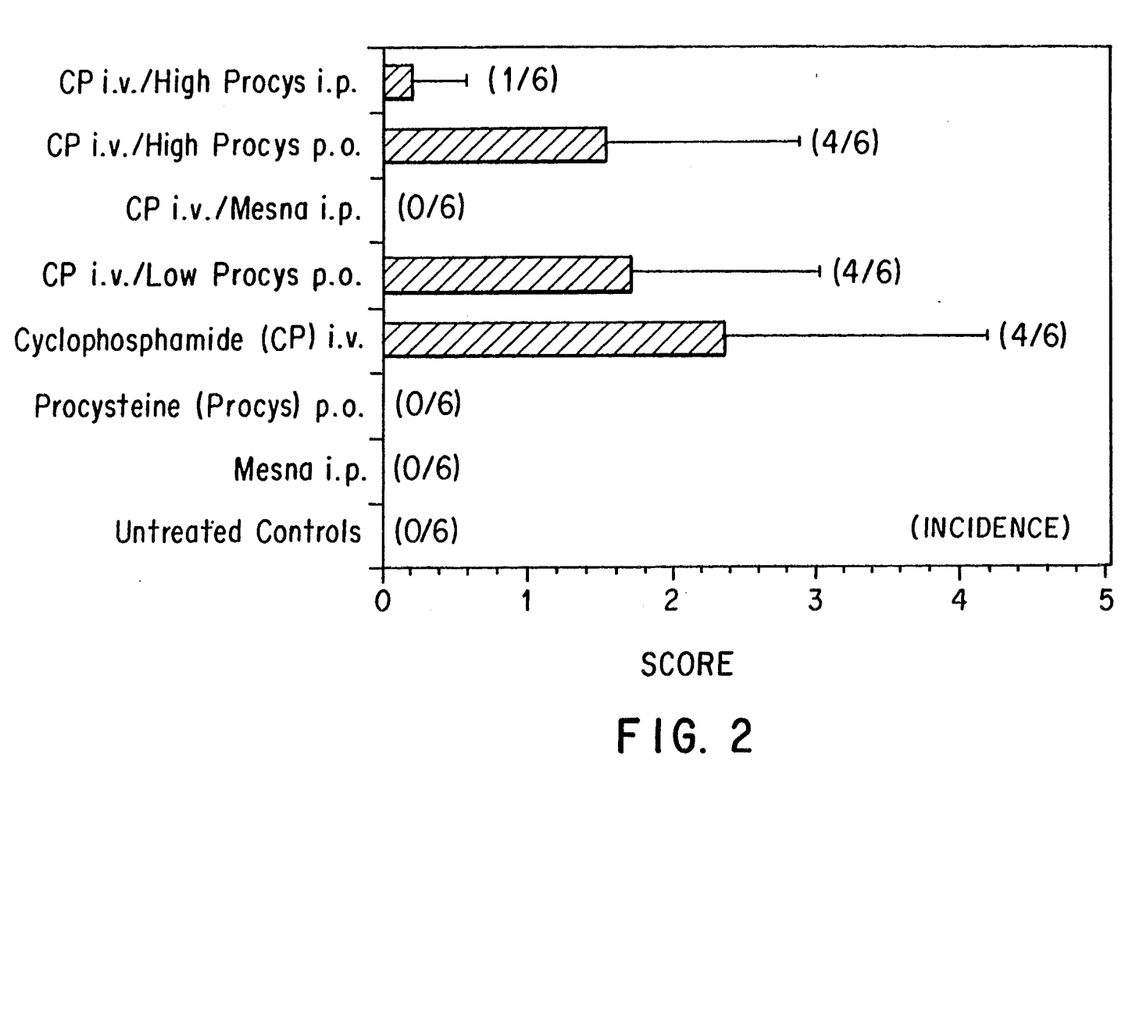

In addition to testing hematology parameters, bladder histology parameters were evaluated. The incidence and severity of cyclophosphamide-induced cystitis was reduced in all co-treatment groups. FIG. 2 illustrates the cystitis severity scores and incidence for each of the eight rat groups.

Expected depression in blood cell parameters were identified in all groups receiving cyclophosphamide with no differences noted between groups. Histologic changes (cystitis) were identified in the bladders of the cyclophosphamide and cyclophosphamide plus Procysteine ® groups. Lesions of the cyclophosphamide plus Procysteine ® were found to be somewhat less severe than the cyclophosphamide alone group when low dose Procysteine ® was given. Higher dosages of Procysteine ® resulted in a significant decrease in lesion incidence and severity.

Procysteine ® protected the bladder epithelium against cyclophosphamide induced cystitis in a similar fashion to Mesna. Immediate cyclophosphamide-induced immunosuppression was maintained as indicated by the reduction of all circulating white blood cells. Cystitis protection by Procysteine ® proved to be dose and administration route dependent as the high dose, intraperitoneal dose was found to be more effective than the two oral dose levels.

Figure 3:
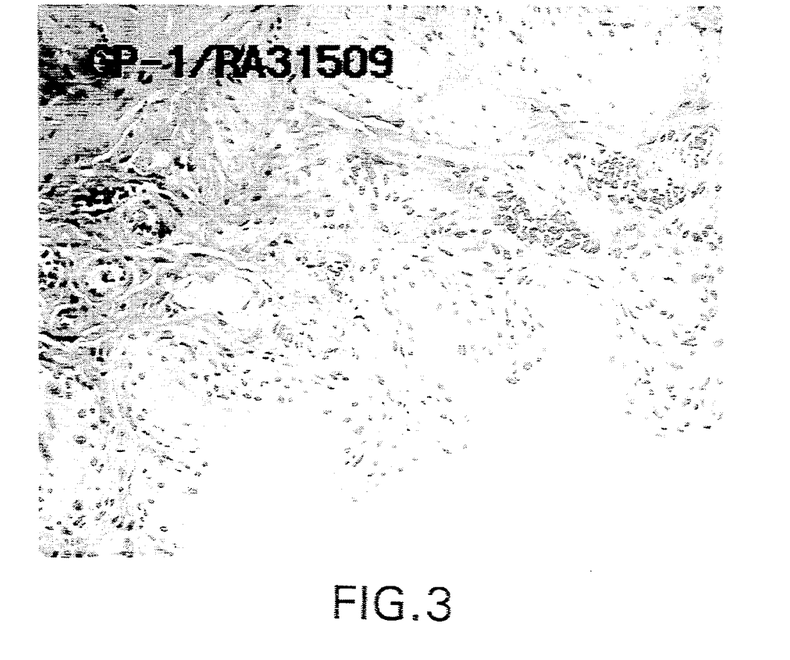
FIGS. 3-6 are photomicrographs representative of bladder walls for various rats treated in an experiment of the present invention.

FIGS. 3–6 are photomicrographs representative of the bladder wall of the rats in the tested groups. FIG. 3 is a photomicrograph (125x) representative of the bladder wall of Group 1, untreated control; Group 2, Mesna alone; and Group 3, Procysteine ® alone. The tissue is normal in appearance.

Figure 4:
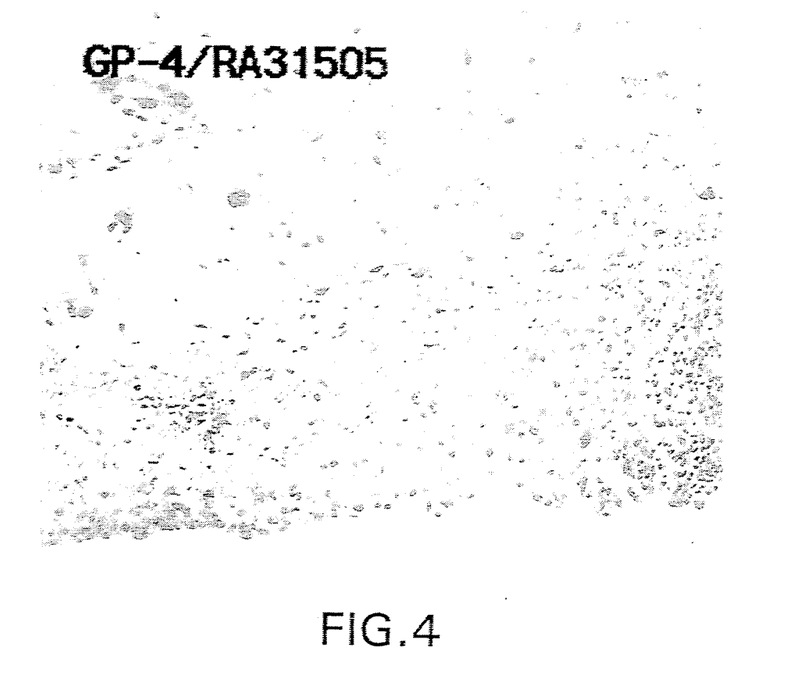

FIG. 4 is a photomicrograph (125x) representative of the bladder wall of Group 4, cyclophosphamide only. Submucosal edema, focal neutrophilic infiltrate, focal hemorrhage, and focal epithelial hyperplasia are seen. These conditions are characteristic of moderate to severe acute cyclophosphamide induced cystitis.

Figure 5:
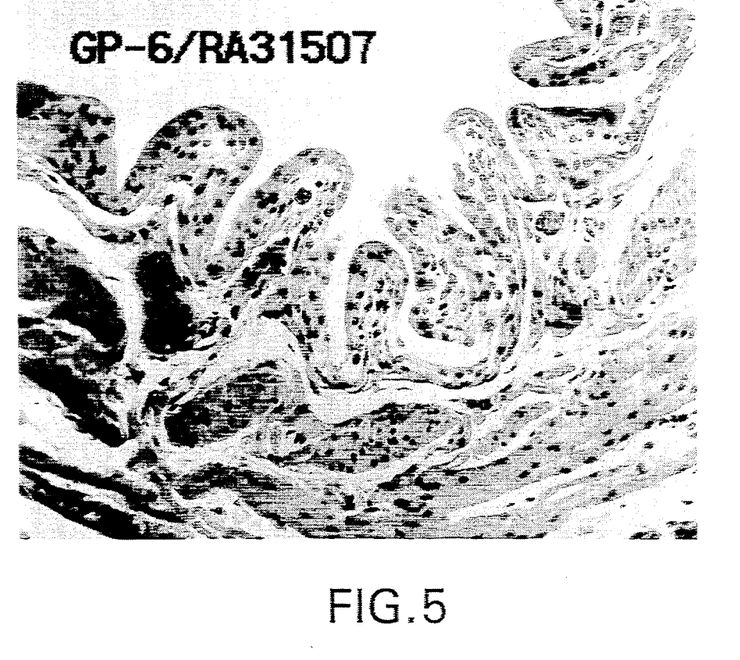

FIG. 5 is a photomicrograph (125x) representative of the bladder wall of Group 6, cyclophosphamide/Mesna co-treatment. Similar to FIG. 4, the tissue again appears normal.

Figure 6:
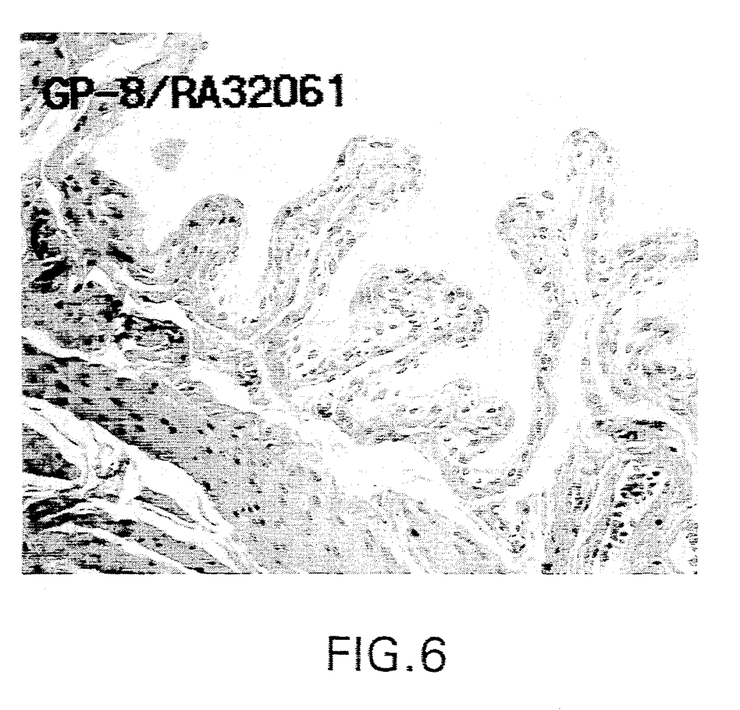

FIG. 6 is a photomicrograph (125x) representative of the bladder wall of Group 8, cyclophosphamide/Procysteine ® (1 g/kg i.p.) group. The tissue again is normal in appearance.

In conclusion, treatment with Procysteine ® ameliorated cyclophosphamide induced hemorrhagic cystitis. Procysteine ® reduced the incidence and severity of cyclophosphamide induced lesions in the bladder.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

We claim:

1. A method for reducing cyclophosphamide induced hemorrhagic cystitis in a patient at risk of same comprising the step of administering to the patient a therapeutically effective amount of a composition including L-2-oxothiazolidine-4-carboxylate.

2. The method of claim 1 wherein the composition is administered parenterally.

3. The method of claim 1 wherein the composition is administered enterally.

4. A method for treating cyclophosphamide induced hemorrhagic cystitis comprising the step of administering to a patient having hemorrhagic cystitis a therapeutically effective amount of a composition including L-2-oxothiazolidine-4-carboxylate.

5. The method of claim 4 wherein the composition is administered parenterally.

6. The method of claim 4 wherein the composition is administered enterally.

7. A method for reducing the hematologic side effects suffered by a patient receiving cyclophosphamide comprising the step of administering to the patient a therapeutically effective amount of a composition including L-2-oxothiazolidine-4-carboxylate.

8. The method of claim 7 wherein the composition is administered parenterally.

9. The method of claim 7 wherein the composition is administered enterally.

10. The method of claim 7 wherein the composition is administered contemporaneously with the cyclophosphamide.

11. The method of claim 7 wherein the composition is administered on the same day the cyclophosphamide is administered.

12. A method for providing chemotherapy to a patient comprising the steps of administering a chemotherapeutic agent that could cause hemorrhagic cystitis to a patient requiring same and a sufficient amount of a composition including L-2-oxothiazolidine-4-carboxylate to reduce hemorrhagic cystitis caused by said chemotherapeutic agent.

13. The method of claim 12 wherein the composition is administered parenterally.

14. The method of claim 12 wherein the composition is administered enterally.

15. The method of claim 12 wherein the chemotherapeutic drug is cyclophosphamide.

16. The method of claim 15 wherein the compositions is administered contemporaneously with the cyclophosphamide.

17. The method of claim 15 wherein the composition is administered on the same day the cyclophosphamide is administered.

* * * * *